United States Patent [19]

Shaffar

[11] 4,252,896

[45] Feb. 24, 1981

[54] METHOD OF STABILIZING PEROXIDASE IN A SERUM PROTEIN BASED MEDIUM

[75] Inventor: Mark R. Shaffar, Park City, Ill.

[73] Assignee: Abbott Laboratories, North Chicago, Ill.

[21] Appl. No.: 110,429

[22] Filed: Jan. 7, 1980

[51] Int. Cl.³ .................. C12Q 1/66; C12Q 1/28; C12N 9/96
[52] U.S. Cl. ........................................ 435/7; 435/28; 435/188
[58] Field of Search ............... 435/7, 28, 188, 253

[56] References Cited

U.S. PATENT DOCUMENTS

| | | | |
|---|---|---|---|
| 3,911,096 | 10/1975 | Chopra | 23/230 B X |
| 3,928,553 | 12/1975 | Hollander | 23/230 B X |
| 4,049,499 | 9/1977 | Lepp et al. | 435/253 X |
| 4,169,012 | 9/1979 | Dawson et al. | 435/7 |

*Primary Examiner*—Robert J. Warden
*Attorney, Agent, or Firm*—Neal O. Willmann

[57] ABSTRACT

The addition of 8-anilino-1-napthalene sulfonic acid to a reagent comprising peroxidase in a serum protein based medium improves the stability of the enzyme 10–20 fold by blocking heme binding proteins and thereby maintaining the structural integrity of the enzyme.

4 Claims, No Drawings

METHOD OF STABILIZING PEROXIDASE IN A SERUM PROTEIN BASED MEDIUM

BACKGROUND OF THE INVENTION

1. Field of the Invention

The invention described in this disclosure relates to and is particularly useful in preparing and storing reagents employed in enzyme immunoassays. In particular, the claimed invention is useful for stabilizing enzymes and enzyme conjugates which are used to detect and determine immunoreactants such as antigens, antibodies, binding proteins and haptens.

2. Description of the Prior Art

Chopra and Hollander both describe in U.S. Pat. Nos. 3,911,096 and 3,928,553, respectively, the usefulness of 8-anilino-1-napthalene sulfonic acid (ANS) as a "blocking agent" to inhibit the binding of triiodothyronine and/or thyroxine to thyroxine binding globulin. The reference patents point out that unextracted serum can be assayed for $T_3$ and/or $T_4$ without the interference of $T_4$ binding globulin and thyroxine binding prealbumin by using a blocking agent such as ANS. The theory of utility, of course, is that the $T_3$ and $T_4$ binding sites on the binding globulin and prealbumin are occupied or blocked by ANS and the $T_3$ and/or $T_4$ are unbound and available for detection by an assay procedure.

U.S. Pat. No. 4,169,012 issued to Dawson, et al describes a method of stabilizing peroxidase compositions by adding polyvalent ions of groups 3 and 4 of the Periodic Table to reagents containing peroxidase compositions. The patentees of this method elaborate on their invention by alleging that reagents stabilized according to their method are particularly amenable to lyophilization.

SUMMARY OF THE INVENTION

A method of stabilizing reagents containing a peroxidase or peroxidase conjugates which are particularly useful in enzymeimmunoassays for the detection and determination of immunoreactants is disclosed. Essentially the claimed method comprises adding to the peroxidase reagent a stabilizingly-effective amount of 8-anilino-1-napthalene sulfonic acid (ANS).

DESCRIPTION OF THE PREFERRED EMBODIMENT

It has been known that peroxidases, whether or not coupled to another component (conjugated), are not very stable, particularly in low concentrations. As a result, their storage stability is rather poor and, therefore, commercial appeal is diminished.

Peroxidases are enzymes which catalyse the oxidation of certain compounds, during which oxidation a peroxidase, in particular hydrogen peroxide, functions as an "acceptor" from a protron donor molecule. Peroxidases may be obtained from plants, for example, horse radish peroxidase (HPO); from vertebrate animals, for example, lactoperoxidase; and from microorganisms such as cytochcome peroxidase from *Pseudomonas*.

Peroxidases are used for a variety of purposes including detectable markers in immunological methods for the detection and determination of immunoreactants, such as haptens, antigens or antibodies. The use of peroxidase labeled immunoreactants is particularly appealing because the activity or presence of the enzyme may be detected visually and degrees of activity may be discerned by colorimetric means.

Assay kits which are marketed for the performance of enzymeimmunoassays usually contain as an essential constituent a certain amount of an immunoreactant coupled to a peroxidase. Since these kits will be subject to shipping and storing for variable lengths of time before use, it is essential that the activity of the enzyme be maintained as long as possible.

Currently the enzyme conjugates are stored in an immunological reaction medium of about 10% fetal calf serum. It has been noted that calf serum contributes to the stability of the conjugate when compared to the stability of the conjugate alone. It is theorized that the serum matrix contributes to maintaining the spacial structure of the enzyme.

Paradoxically, it has also been observed that the calf serum contributes to the inactivation of the enzyme by extracting detachable hemin moieties from the enzyme structure. This denaturation of peroxidase appears to be due to hemin interactions between the peroxidase and hemin binding proteins from the calf serum.

In order to diminish the attraction and therefore the interaction between hemin and serum proteins, it has been found that adding ANS to the reagent medium improves the stability of the peroxidase 10-20 fold. It is believed that ANS improves stability of the peroxidase by reacting with serum proteins in the calf serum and occupying heme binding sites.

The following elaboration will demonstrate the utility of the claimed invention:

EXAMPLE

Commercially available fetal calf serum was pooled and heat treated at 55° C. for one hour to remove any endogenous peroxidative activity. The serum was filtered through an ertel pad to remove any precipitates and the filtrate was diluted with 0.1 M tris buffer (pH 7.5) and 0.15 M NaCl to provide a final concentration of 10% serum. The serum composition was poured into two individual vials. To one via was added 8-anilino-1-napthalene sulfonic acid providing a concentration of 0.01%. Horse radish peroxidase, conjugated to IgG by periodate oxidation, was added to each buffered serum solution. All solutions were filtered through a 0.45$\mu$ sterile filter and aliquoted to 5 ml sterile bottles. The bottles were then stored at 4° C. or 45° C.

The contents of each bottle was assayed for enzyme activity to determine stability at 0, 8, 20, and 43 days. Enzyme activity was determined spectrophotometrically on a bichromatic analyzer at 415 nm. A five-minute rate analysis was conducted by mixing 10 $\mu$l of the enzyme solution with 250 $\mu$l of a substrate solution containing phosphate tris buffer, pH 6, hydrogen peroxide, and 3 mg/ml of o-phenylene diamine. Stability was determined by calculating the percent enzyme activity at 45° storage relative to the activity demonstrated by enzyme stored at 4° C.

The following chart illustrates the results of said study:

| Stabilizer | Relative Enzyme Activity | | | |
|---|---|---|---|---|
| | 0 days | 7.5 days | 19.5 days | 43 days |
| None | 100% | 7.5% | 2.4% | 0% |
| 0.01% ANS | 100% | 77% | 66% | 43% |

I claim:

1. A method of stabilizing peroxidase in a serum protein based medium which comprises adding to said medium an effective amount of 8-anilino-1-napthalene sulfonic acid.

2. A method according to claim 1 wherein the 8-anilino-1-napthalene sulfonic acid is employed in a concentration of about 0.001% to about 0.5%.

3. A method of stabilizing horse radish peroxidase in fetal calf serum which comprises adding to said medium an effective amount of 8-anilino-1-napthalene sulfonic acid.

4. A reagent useful in immunochemical determinations which comprises a peroxidase in a serum protein based medium stabilized with 8-anilino-1-napthalene sulfonic acid.

* * * * *